(12) United States Patent
Karmaker et al.

(10) Patent No.: US 6,381,989 B1
(45) Date of Patent: May 7, 2002

(54) HEAT TREATED FIBERS FOR REINFORCED DENTAL RESTORATIONS AND METHOD OF MANUFACTURE THEREOF

(75) Inventors: Ajit Karmaker, Wallingford; Arun Prasad, Cheshire, both of CT (US)

(73) Assignee: Jeneric/Pentron Incorporated, Wallingford, CT (US)

( * ) Notice: Subject to any disclaimer, the term of this patent is extended or adjusted under 35 U.S.C. 154(b) by 0 days.

(21) Appl. No.: 09/642,727

(22) Filed: Aug. 21, 2000

Related U.S. Application Data

(60) Continuation of application No. 09/292,479, filed on Apr. 15, 1999, now abandoned, which is a division of application No. 08/936,361, filed on Sep. 24, 1997, now Pat. No. 6,030,220.

(51) Int. Cl.[7] .............................................. C03B 37/07
(52) U.S. Cl. .............................. 65/384; 65/376; 65/438; 65/441; 65/442; 65/117; 501/35; 501/36; 501/55; 501/59; 433/215; 433/180; 433/167; 139/420 C
(58) Field of Search .......................... 65/376, 384, 438, 65/441, 442, 488, 504, 507, 480, 408, 117; 501/35, 36, 55, 59; 433/215, 180, 167; 139/420 C

(56) References Cited

U.S. PATENT DOCUMENTS

| | | | |
|---|---|---|---|
| 4,107,845 A | 8/1978 | Lee, Jr. et al. | |
| 4,172,323 A | 10/1979 | Orlowski | |
| 4,433,960 A | 2/1984 | Garito et al. | |
| 4,717,341 A | 1/1988 | Goldberg et al. | |
| 4,728,291 A | 3/1988 | Golub | |
| 4,799,888 A | 1/1989 | Golub | |
| 4,867,683 A | 9/1989 | Meisel | |
| 4,894,012 A | 1/1990 | Goldberg et al. | |
| 5,000,687 A | 3/1991 | Yarovesky et al. | |
| 5,015,180 A | 5/1991 | Randklev | |
| 5,074,791 A | 12/1991 | Shoher et al. | |
| 5,098,304 A | 3/1992 | Scharf | |
| 5,120,224 A | 6/1992 | Golub | |
| 5,176,951 A | 1/1993 | Rudo | |
| 5,829,979 A | 11/1998 | Kubashigawa et al. | |

FOREIGN PATENT DOCUMENTS

| | | |
|---|---|---|
| FR | 2146216 | 3/1973 |
| FR | 1178322 | 5/1979 |
| FR | 2416074 | 8/1979 |

OTHER PUBLICATIONS

Search Report for EP 98 11 7695 (U.S.S.N. 08/936,361).

*Primary Examiner*—Michael Colaianni
(74) *Attorney, Agent, or Firm*—Cantor Colburn LLP

(57) ABSTRACT

A method for processing a glass fiber material, wherein the glass fiber material has been heat treated at a temperature less than or equal to the annealing temperature of the glass for a length of time effective to prevent separation and fraying of the edges of the material upon cutting.

7 Claims, 3 Drawing Sheets

HEAT TREATED FIBERS FOR REINFORCED DENTAL RESTORATIONS AND METHOD OF MANUFACTURE THEREOF

CROSS-REFERENCE TO RELATED APPLICATION

This application claims priority to and is a continuation of U.S. patent application Ser. No. 09/292,479 for HEAT TREATED FIBERS FOR REINFORCED DENTAL RESTORATIONS AND METHOD OF MANUFACTURE THEREOF, filed Apr. 15, 1999 by Ajit Karmaker et al., now abandoned, which claims priority to and is a division of U.S. patent application Ser. No. 08/936,361 for HEAT TREATED FIBERS FOR REINFORCED DENTAL RESTORATIONS AND METHOD OF MANUFACTURE THEREOF, filed Sep. 24, 1997 by Ajit Karnaker et al., now U.S. Pat. No. 6,030,220.

BACKGROUND OF THE INVENTION

1. Field of the Invention

This invention relates to dental restorations and methods of manufacture thereof. In particular, this invention relates to splints, laminates, veneers, and dental bridges comprising glass fiber reinforcement, wherein the reinforcing glass fibers have been heat treated to prevent fraying and separation of the fibers.

2. Brief Discussion of the Prior Art

Fiber-reinforced composites have found increasing use in the field of materials for dental restorations, and are described, for example, in U.S. Pat. Nos. 4,717,341 and 4,894,012 to Goldberg et al., as well as U.S. Pat. No. 4,107,845 to Lee, Jr. et al. Fiber-reinforced composites generally comprise at least two components, a polymeric matrix and fibers embedded within the matrix. The composite materials may further comprise a filler material. Common polymeric matrices include those known for use in composite dental materials, for example polyamides, polyesters, acrylates, polyolefins, polyimides, polyarylates, polyurethanes, vinyl esters, or epoxy-based materials. Other polymeric matrices include styrenes, styrene acrylonitriles, ABS polymers, polysulfones, polyacetals, polycarbonates, polyphenylene sulfides, and the like. The fibers used to reinforce composite material may comprise glass, carbon, or polymer fibers such as polyaramide and polyethylene, as well as other natural and synthetic fibers.

Fiber-reinforced composite materials provide several advantages, most notably increased strength and stiffness. As described in U.S. Pat. Nos. 4,717,341 and 4,894,012 to Goldberg et al., such materials may be used as structural components in a variety of dental appliances, taking the form of bars, wires, beams, posts, clasps, and laminates. The fibers preferably take the form of long, continuous filaments, although the filaments may be as short as 3 to 4 millimeters. Where the composites take the form of elongated wires, the fibers are at least partially aligned and oriented along the longitudinal dimensions of the wire. However, depending on the end use of the composite material, the fibers may also be otherwise oriented, including being normal or perpendicular to that dimension. These structural components are used in traditional bridges, crowns, artificial teeth, dentures, implants, veneers, as well as in connection with orthodontic retainers, space maintainers, splints, and the like.

A bridge, in particular, is a device for the restoration and replacement of one or more natural teeth, replacing at least one missing tooth and supported on either side by the remaining (abutment) teeth. A bridge generally comprises a pontic for replacement of the missing tooth, and a connector which connects the pontic to a retaining member, such as a crown formed on an abutment tooth adjacent the pontic. By their nature, bridges must be aesthetic, as well as strong, in order to withstand forces generated by chewing and to maintain the positions of the abutting teeth. A number of bridge designs disclosed in the prior art are intended to either enhance strength or ease of preparation. For example, U.S. Pat. No. 5,074,791 discloses a bridge comprising a preformed pontic, which simplifies preparation. The so-called "winged bridge" disclosed in U.S. Pat. No. 5,000,687 is designed to enhance bridge strength by providing extensions ("wings") on the pontic which are adhered to the distal side of the abutment teeth. Woven fiber reinforcement of dental bridges is also disclosed in U.S. Pat. No. 4,728,291, U.S. Pat. No. 4,799,888 and U.S. Pat. No. 5,120,224, all to Golub; U.S. Pat. No. 5,098,304 to Scharf; and U.S. Pat. No. 5,176,951 to Rudo.

Other related devices that may use fiber-reinforced composites include splints, laminates, and veneers. Splints are used to provide strength and stability to loose teeth, or to temporary replacement teeth. Laminates and veneers may cover one or more teeth, and are used for aesthetic purposes. Fiber-reinforced splints, laminates, and veneers are described in the above-mentioned patents to Golub and Scharf.

While it is well known in the art to use a woven glass fabric as the fiber component of fiber-reinforced composites, a significant drawback has been the tendency of yarns of a woven and nonwoven glass fabric to fray, that is to separate from the fabric when the fabric is cut. Fraying of the yarns, especially at the ends of the cut fabric, presents difficulties in the processing and use of the fabric. Glass fabric is especially prone to fraying, which severely restricts its use. Accordingly, there remains a need for a glass fiber material that may be processed without fraying and separation of the fibers after the glass fiber fabric has been cut.

SUMMARY OF THE INVENTION

The above-described and other problems and deficiencies of the prior art are overcome or alleviated by the heat treated glass fiber material of the present invention, wherein the glass fiber material has been heat treated at a temperature less than or equal to the annealing temperature of the glass. The glass fiber material may be a uniform mesh, a random mesh, or a rope, tape or thread type material. Particularly preferred for use in the present invention is a woven glass fabric material. Heat treatment of the glass fiber material prior to cutting prevents fraying of the edges upon cutting, which greatly enhances ease of preparation of the fiber-reinforced restorations.

BRIEF DESCRIPTION OF THE DRAWINGS

For the purpose of illustrating the invention, there are shown in the drawing forms which are presently preferred; it being understood, however, that this invention is not limited to the precise arrangements and instrumentalities shown. Referring now to the drawings wherein like elements are numbered alike in the several FIGURES.

DETAILED DESCRIPTION OF THE INVENTION

The present invention is directed to a new and improved means and method for reinforcing dental restorations and/or splinting teeth, wherein the reinforcing glass fiber material is heat treated. In accordance with the present invention, a glass fiber material is heated to a temperature equal to or less than the annealing temperature prior to cutting. The glass fiber material is heated for a time period effective to prevent fraying and separation of the edges of the material when the material is cut. Any method of cutting known in the art may be employed to cut the glass fiber material. The fiber-reinforced composites generally comprise at least two components, a polymeric matrix and fibers embedded within the polymeric matrix. The polymeric matrix may further comprise fillers known in the art.

Heat Treatment of the Glass Fiber Material

Figure 1:
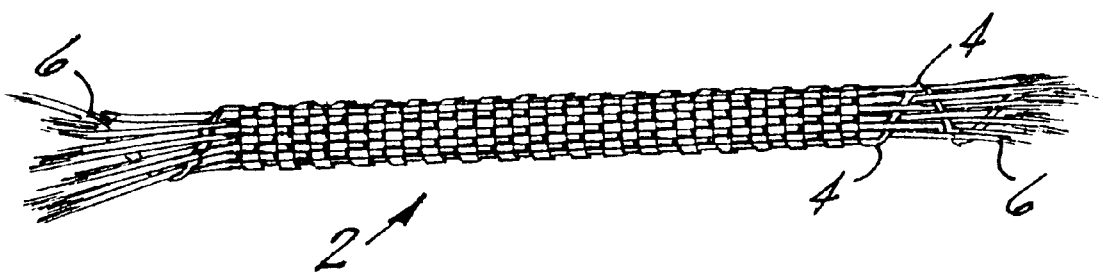
FIG. 1 is a plan view of a prior art woven tape comprising glass fibers, which has been cut without prior heat treatment of the fibers.

In accordance with the present invention, the glass fiber material is heated prior to its cutting and application to the polymeric matrix component of the composite material. As previously described, one drawback to the use of glass fiber materials has been the tendency of fibers of the material to separate when it is cut. A prior art uniform mesh woven tape 2 comprising glass fibers 4 which has been cut without prior heat treatment of the fibers is shown in FIG. 1, illustrating the fraying 6 that occurs upon cutting.

Without being bound by theory, it is hypothesized that the fraying is caused by the bending of the glass fibers. In a woven fabric, the yarns in the y-direction are called warp yarns, and represent the length of the fabric. The yarns in the x-direction are called fill yarns and represent the width of the fabric. When the woven glass fabric is in the shape of a narrow tape, the tendency for the fill yarn to separate from the fabric is increased and consequently, the narrow tape separates at its ends upon cutting. This is probably because the fill yarn of the fabric is mechanically bent at its turning points during weaving at both edges of the tape. The bending of the fibers is still within the elastic region of the glass, and the fibers tend to regain their original positions when the fabric is cut. Consequently, the tape frays at its ends.

Figure 2:
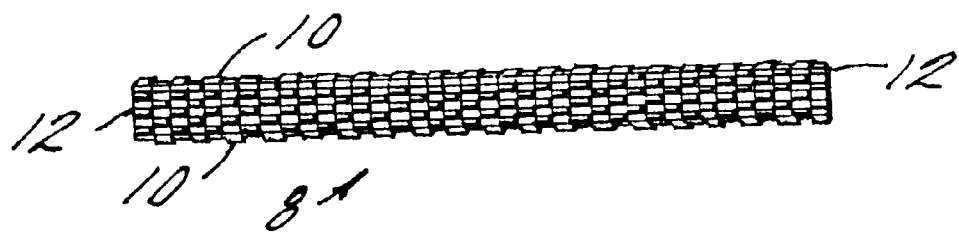
FIG. 2 is a plan view of a woven tape comprising glass fibers, which has been cut after heat treatment of the glass fibers in accordance with the present invention.

This problem associated with the cutting of the glass fiber material is overcome or alleviated by the heat treatment of the glass fiber material prior to the cutting of the glass fiber material. FIG. 2 illustrates a uniform mesh woven tape 8 comprising glass fibers 10 which has been cut after heat treatment of the glass fibers in accordance with the present invention. The ends of the tape 12 are substantially unfrayed after cutting. In accordance with the present invention, the glass fiber material is heated at a temperature equal to or less than the annealing temperature of the material. The annealing temperature of commercially available glass fiber can vary in the range from about 400° C. to about 800° C., depending on the chemical compositions. For example, the annealing temperature for S-glass fiber is about 800° C., whereas for E-glass fiber it is only about 650° C.

The duration time of the heat treatment is empirically determined and will depend upon the temperature selected for the heat treatment process. The duration time can be from several minutes to several hours, but must be sufficient to result in glass fibers which do not separate or unravel when cut. For example, at a temperature of 600° C. the treatment time for plain woven E-glass tape would be less than 5 minutes. If the temperature is 400° C., the material needs to be treated for several hours to get the same effect. Again, without being bound by theory, it is hypothesized that the instant heat treatment relieves internal stresses which originally remained in the fiber and which built up during bending at the turning points.

Glass Fibers

Figure 3:
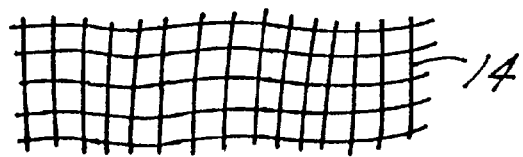
FIG. 3 is a plan view of a uniform mesh comprised of glass fibers which may be utilized in the present invention.
Figure 4:
FIG. 4 is a plan view of random mesh comprised of glass fibers which may be utilized in practicing the present invention.
Figure 5:
FIG. 5 is a plan view of woven thread or rope comprised of glass fibers which may be utilized in the present invention.

In accordance with the present invention, a glass fiber material is used for reinforcement of the composite. The glass fiber material is preferably in the form of a woven tape as shown in FIGS. 1 and 2, but may also be in any form that frays upon cutting. FIG. 3 illustrates a uniform mesh 14 comprising glass fibers, and FIG. 4 illustrates a random mesh 16 comprising glass fibers, and FIG. 5 illustrates a woven thread or rope 18 comprising a glass fiber material. The glass fiber material is a strong material which provides significant improvement to the strength of the composite resin.

Suitable glasses include those known in the art, including but not being limited to the compositions set forth in the Table below. A preferred glass formulation is known in the art as "E Glass". A suitable tape of E glass is available from Omnia LLC, Raleigh, N.C., under the designation Ribbon, Glass Fiber, Style 711.

| Oxide* | A-Glass | C-Glass | D-Glass | E-Glass | ECR-Glass | AR-Glass | R-Glass | S-2Glass ® |
|---|---|---|---|---|---|---|---|---|
| $SiO_2$ | 63–72 | 64–68 | 72–75 | 52–56 | 54–62 | 55–75 | 55–65 | 64–66 |
| $Al_2O_3$ | 0–6 | 3–5 | 0–1 | 12–16 | 9–15 | 0–5 | 15–30 | 24–25 |
| $B_2O_3$ | 0–6 | 4–6 | 21–24 | 5–10 | | 0–8 | | |
| CaO | 6–10 | 11–15 | 0–1 | 16–25 | 17–25 | 1–10 | 9–25 | 0–0.1 |
| MgO | 0–4 | 2–4 | | 0–5 | 0–4 | | 3–8 | 9.5–10 |
| ZnO | | | | | 2–5 | | | |
| BaO | | 0–1 | | | | | | |
| $Li_2O$ | | | | | | 0–1.5 | | |
| $Na_2O + K_2O$ | 14–16 | 7–10 | 0–4 | 0–2 | 0–2 | 11–21 | 0–1 | 0–0.2 |

-continued

| Oxide* | A-Glass | C-Glass | D-Glass | E-Glass | ECR-Glass | AR-Glass | R-Glass | S-2Glass ® |
|---|---|---|---|---|---|---|---|---|
| TiO₂ | 0–0.6 | | | 0–1.5 | 0–4 | 0–12 | | |
| ZrO₂ | | | | | | 1–18 | | |
| Fe₂O₃ | 0–0.5 | 0–0.8 | 0–0.3 | 0–0.8 | 0–0.8 | 0–5 | | 0–0.1 |
| F₂ | 0–0.4 | | | 0–1 | | 0–5 | 0–0.3 | |
| Annealing point, ° C. | | 588 | 521 | 657 | | | | 816 |

*percent by weight

In order to enhance the bonding of the glass fiber material to the polymeric matrix, the glass fiber material may be first etched and then treated with an organo-functional silane prior to the application to the polymeric matrix by methods known in the art. The etching of the glass fibers produces a roughened or barbed surface, which may be observed under a microscope. After the etching is completed, any suitable organo-functional silane may be utilized which is capable of enhancing the bonding between the glass fiber material and the polymeric matrix. Alternatively, the glass fibers may be silanated without etching. A number of silanizing agents are well known and examples of these include the following: vinyltrichlorosilane, vinyltriethoxysilane, vinyl-tris(beta-methoxyethoxy)silane, gamma-methacryloxypropyltrimethoxysilane, beta-(3,4-epoxycyclohexyl)-ethyltrimethoxysilane, gamma-glycidoxypropyltrimethoxysilane, gamma-aminopropyltriethoxysilane, and N-beta(aminoethyl)-gamma-aminopropyltrimethoxysilane.

Polymeric Matrix

The polymeric matrix is selected from those known in the art of dental materials, including but not being limited to polyamides, acrylates, polyesters, polyolefins, polyimides, polyarylates, polyurethanes, vinyl esters or epoxy-based materials. Other polymeric matrices include styrenes, styrene acrylonitriles, ABS polymers, polysulfones, polyacetals, polycarbonates, polyphenylene sulfides, and the like.

Preferred materials include those based on acrylic and methacrylic monomers, for example those disclosed in U.S. Pat. No. 3,066,112, U.S. Pat. No. 3,179,623, and U.S. Pat. No. 3,194,784 to Bowen; U.S. Pat. No. 3,751,399 and U.S. Pat. No. 3,926,906 to Lee et al.; and commonly assigned U.S. Pat. No. 5,276,068 to Waknine, all of which are herein incorporated by reference in their entirety. An especially preferred methacrylate monomer is the condensation product of bisphenol A and glycidyl methacrylate, 2,2'-bis[4-(3-methacryloxy-2-hydroxy propoxy)-phenyl]-propane (hereinafter abbreviated "BIS-GMA"). Polyurethane dimethacrylates (hereinafter abbreviated to PUDMA) are also commonly-used principal polymers suitable for use in the present invention.

The polymeric matrix may further comprise a co-polymerizable diluent monomer. Such monomers are generally used to adjust the viscosity of the polymerizable composition, which affects wettability of the composition. Suitable diluent monomers include, without limitation, hydroxyalkyl methacrylates, such as 2-hydroxyethylmethacrylate, 1,6-hexanedioldimethacrylate, and 2-hydroxypropylmethacrylate; glyceryl dimethacrylate; ethyleneglycolmethacrylates, including ethyleneglycolmethacrylate, diethyleneglycolmethacrylate, triethyleneglycolmethacrylate and tetraethyleneglycolmethacrylate; and diisocyanates, such as 1,6-hexamethylene diisocyanate. Triethyleneglycoldimethacrylate (TEGDMA) is particularly preferred for use in the present invention.

The polymer matrix typically includes polymerization initiators, polymerization accelerators, ultra-violet light absorbers, anti-oxidants, fluorescent whitening agents, and other additives well known in the art. The polymer matrices may be visible light curable, self-curing, dual curing, and vacuum, heat, and pressure curable compositions as well as any combination thereof. Visible light curable compositions employ light-sensitive compounds such as benzil diketones, and in particular, dl-camphoroquinone in amounts ranging from about 0.05 to 0.5 weight percent. UV absorbers are particularly desirable in the visible light curable compositions in order to avoid discoloration of the resin form any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y. in amounts ranging from about 0.05 to about 5.0 weight percent.

In the self-curing compositions, a polymerization accelerator may be included in the polymerizable monomer composition. The polymerization accelerators suitable for use include the various organic tertiary amines well known in the art, generally aromatic tertiary amines, such as dimethyl-p-toluidine, dihydroxyethyl-p-toluidine and the like, in amounts ranging from about 0.05 to about 4.0 weight percent, and generally acrylate derivatives such as dimethylaminoethyl methacrylate and particularly, diethylaminoethyl methacrylate in amounts ranging from about 0.05 to 0.5 weight percent.

The heat and pressure curable compositions, which are generally filled compositions, include, in addition to the monomeric components, a heat cure initiator such as benzoyl peroxide, 1,1'-azobis(cyclohexanecarbo-nitrile), or other free radical initiators. Particularly suitable free radical initiators are lauroyl peroxide, tributyl hydroperoxide and, more particularly benzoyl peroxide.

In addition to unfilled polymeric matrices, the polymeric matrices of the present invention can also be filled or partially filled. The filled compositions of the invention can include all of the inorganic/organic fillers currently used in dental restorative materials, the amount of such filler being determined by the specific function of the filled materials.

The filled compositions of this invention can, in general, include any suitable filler which is capable of being covalently bonded to the polymer matrix itself or to a coupling agent which is covalently bonded to both. Examples of suitable filling materials include but are not limited to, silica, silicate glass, quartz, barium silicate, strontium silicate, barium borosilicate, strontium borosilicate, borosilicate, lithium silicate, amorphous silica, ammoniated or deammoniated calcium phosphate, and alumina zirconia tin oxide and titania. Particularly suitable fillers for dental filling-type materials prepared in accordance with this invention are those having a particle size ranging from about 0.1 to 5.0 µm with a silicate colloid of 0.001 to about 0.07 microns. These are prepared by a series of milling steps comprising wet milling in an aqueous medium, surface etch milling and silanizing milling in a silane solution. Some of the aforementioned inorganic filling materials are disclosed in U.S. Pat. No. 4,544,359 and U.S. Pat. No. 4,547,531, pertinent portions of which are incorporated herein by reference. The filler content in general is in the range from about 0 to 85% by weight of the total composition, depending on the use made of the polymerized composition.

One preferred polymeric matrix usable in accordance with the present invention comprises approximately 70% filler material by weight, with the remaining material being BIS-GMA and TEGDMA in a ratio of about 1:1 by weight, and suitable curing agents. This material is commercially available under the trade name FLOW-IT, from JENERIC/PENTRON, Inc. Wallingford, Conn. Another polymeric matrix usable in accordance with the present invention comprises BIS-GMA and PCDMA in a ratio of about 9:1 by weight, and suitable curing agents.

In the practice of the present invention, a polymeric matrix is applied to the restoration site prior to the application of the reinforcing glass fibers. Preferably, the polymeric matrix is uncured and comprises initiators known in the art, for example, camphorquine. The dental restoration site may be an untreated or pretreated enamel or dentin surfaces, or an untreated or pretreated porcelain, composite, or metallic surface. The reinforcing glass fiber material is then applied in intimate contact with the polymeric matrix. Additional polymeric matrix (preferably of the same composition as the first applied polymeric matrix) is preferably next applied to the dental restoration at the restoration site. Preferably, the reinforcing glass fiber material is pre-impregnated with a polymeric matrix and not cured before application to the site of the restoration. The impregnating matrix may also be partially or fully cured before application. The applied matrix and impregnating matrix need not be identical, i.e., the applied matrix may be FLOW-IT, while the impregnating matrix may comprise BISGMA-PCDMA in a ratio of about 9:1 by weight. In this case, one or both steps of applying polymeric matrix to the restoration site may be omitted. Non-impregnated glass fiber material may also be used.

The present invention may be utilized in numerous applications in the practice of dentistry, including periodontal splinting, tooth replacement, tooth stabilization, bridge manufacture, and the like. All of these will not be described herein, as such dental operations are well known to those practicing dentistry, i.e. those of ordinary skill in the art. However, an illustration of a few of the possible uses will be illustrated herein in connection with the drawing figures. The operations and specific detail of the actual practice of dentistry will not be repeated herein as they are well known in the art.

Figure 6:
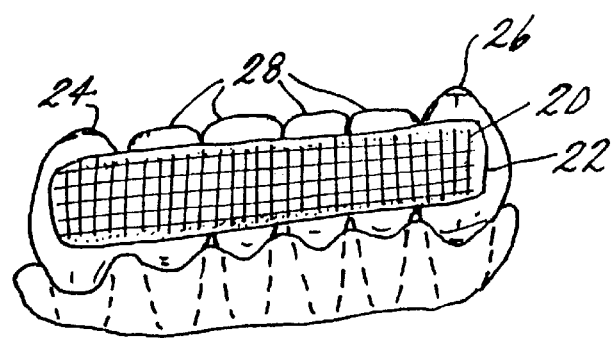
FIG. 6 is an elevation view of periodontal splinting utilizing a glass fiber uniform mesh applied to mandibular anterior teeth illustrating one use of the present invention.

Referring now to the drawings wherein like numerals indicate like elements, in FIG. 6 there is illustrated periodontal splinting of mandibular anterior teeth utilizing a uniform glass fiber mesh 20 which has been heated at a temperature equal to or less than the annealing temperature of the material and embedded within a polymeric matrix material 22. The uniform glass fiber mesh 20 may be etched and treated with an organo-functional silane prior to embedding within the polymeric matrix material 22. As described previously, the glass fiber mesh 20 may be etched with an acid or base which is effective in etching glass fibers and treated with a silane, or simply silanated. The periodontal splinting as shown in FIG. 6 is utilized to treat mobile teeth which have lost bone support and/or which have been traumatized. As illustrated in FIG. 6, the heat treated glass fiber mesh 20 may be embedded in a polymeric matrix material 22 bonding together canines 24 and 26 and mandibular incisors 28.

Figure 7:
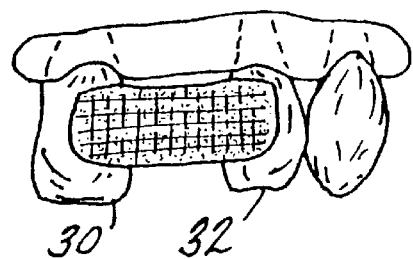
FIGS. 7 and 8 are elevation views of maxillary anterior teeth illustrating steps in tooth replacement utilizing a uniform glass fiber mesh in accordance with the present invention.
Figure 8:
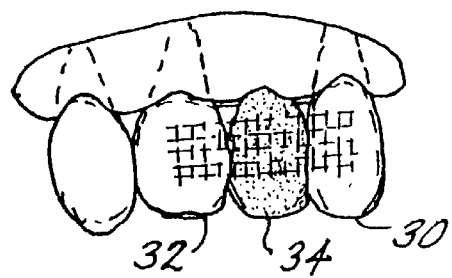

Referring now to FIGS. 7 and 8, there is shown another one of the many possible uses of the present invention in the field of dentistry in the form of an anterior tooth replacement. A polymeric matrix is applied to abutment teeth 30 and 32 which are immediately adjacent the missing tooth. The fiber-reinforced composite comprising a heat treated glass fiber material embedded in a polymer matrix material is provided and applied to the restoration site on teeth 30, 32. Additional polymeric matrix may then be applied to the fiber-reinforced composite. The formation of the replacement tooth 34 is now built into the mesh, polymerized and shaped into the form of a tooth, according to methods known in the art.

As shown and described above, the heat treated glass fiber material in accordance with the present invention is more effectively processed and used in fiber-reinforced dental restorations than prior art materials. The use of a heat treated glass fiber material alleviates the problems associated with the fraying and separation of the edges of the glass fiber material when it is cut.

While preferred embodiments have been shown and described, various modifications and substitutions may be made thereto without departing from the spirit and scope of the invention. Accordingly, it is to be understood that the present invention has been described by way of illustrations and not limitation.

What is claimed is:
1. A method of making a dental restoration comprising:
   applying to a dental restoration site a heat treated glass fiber material formed by:
      providing a glass fiber material which frays upon cutting; and
      heat treating the glass fiber material at a temperature less than its annealing point, for a period of time effective to prevent fraying of the glass fiber material upon cutting of the material.
2. The method of claim 1, wherein the glass fiber material is in the form of a uniform mesh or random mesh.
3. The method of claim 2, wherein the glass fiber material is in the form of a woven mesh, tape, thread, or rope.
4. The method of claim 3, wherein the glass fiber material is in the form of a woven tape.
5. The method of claim 1, wherein the heat treatment is in a range between about 400° C. and 800° C.
6. The method of claim 1, wherein the glass fiber has a composition comprising about 52–56% $SiO_2$, 12–16% $Al_2O_3$, 5–10% $B_2O_3$, 16–25 % CaO, 0–5 % MgO, 0–2% $Na_2O+K_2O$, 0–1.5% $TiO_2$, 0–0.8% $Fe_2O_3$, and 0–1% fluoride.
7. The method of claim 6, wherein the heat treatment is in a range between about 400° C. and about 600° C.

* * * * *

UNITED STATES PATENT AND TRADEMARK OFFICE
CERTIFICATE OF CORRECTION

PATENT NO. : 6,381,989 B1
DATED : May 7, 2002
INVENTOR(S) : Karmaker et al.

It is certified that error appears in the above-identified patent and that said Letters Patent is hereby corrected as shown below:

Column 1,
Line 17, after "Ajit" delete "Karnaker" and insert therefor -- Karmaker --

Signed and Sealed this

Ninth Day of August, 2005

JON W. DUDAS
*Director of the United States Patent and Trademark Office*